United States Patent
Graham

(10) Patent No.: US 9,554,836 B2
(45) Date of Patent: Jan. 31, 2017

(54) INTRAMEDULLARY BONE STENT

(71) Applicant: THE CLEVELAND CLINIC FOUNDATION, Cleveland, OH (US)

(72) Inventor: Thomas J. Graham, Novelty, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

(21) Appl. No.: 13/932,213

(22) Filed: Jul. 1, 2013

(65) Prior Publication Data
US 2014/0005669 A1  Jan. 2, 2014

Related U.S. Application Data

(60) Provisional application No. 61/665,949, filed on Jun. 29, 2012.

(51) Int. Cl.
*A61B 17/72* (2006.01)

(52) U.S. Cl.
CPC ........... *A61B 17/72* (2013.01); *A61B 17/7225* (2013.01); *A61B 17/7233* (2013.01)

(58) Field of Classification Search
CPC . A61B 17/74; A61B 17/1717; A61B 17/8685; A61B 17/921; A61B 17/68; A61B 17/72–17/7291; A61B 17/8645; A61B 17/869
USPC ....................................................... 606/62–64
See application file for complete search history.

(56) References Cited

U.S. PATENT DOCUMENTS

| | | | | |
|---|---|---|---|---|
| 4,762,453 A * | 8/1988 | DeCaro | ................. | E04D 3/3603 411/383 |
| 5,015,248 A * | 5/1991 | Burstein et al. | ................. | 606/74 |
| 5,018,530 A * | 5/1991 | Rank et al. | .................... | 600/562 |
| 5,582,616 A * | 12/1996 | Bolduc et al. | ................. | 606/143 |
| 5,662,683 A * | 9/1997 | Kay | .................... | A61B 17/0401 411/425 |
| 5,837,006 A * | 11/1998 | Ocel et al. | ..................... | 607/127 |
| 5,904,696 A * | 5/1999 | Rosenman | ......... | A61B 17/0401 606/151 |
| 6,149,574 A * | 11/2000 | Trauthen et al. | ................. | 600/3 |
| 6,174,312 B1 * | 1/2001 | Laminger | ........................ | 606/63 |
| 6,468,309 B1 * | 10/2002 | Lieberman | ................. | 623/17.11 |
| 6,656,184 B1 * | 12/2003 | White | ................ | A61B 17/8625 606/318 |
| 6,984,241 B2 * | 1/2006 | Lubbers | ............. | A61B 17/0401 606/103 |

(Continued)

FOREIGN PATENT DOCUMENTS

| DE | 3835682 | * | 4/1990 | ............. A61B 17/58 |
|---|---|---|---|---|
| EP | 0374088 | * | 6/1990 | ............. A61B 17/58 |

OTHER PUBLICATIONS

EP0374088, Jun. 1990, Muller, A61B 17/58, English machine translation document.*

(Continued)

*Primary Examiner* — Jacqueline Johanas
(74) *Attorney, Agent, or Firm* — Tarolli, Sundheim, Covell & Tummino LLP

(57) ABSTRACT

A bone fixation device comprises an elongated body. The elongated body includes a first end portion with a coil and an opposite second end portion with an elongated tail. The second end portion also includes an attachment portion configured for engagement with a fastener.

16 Claims, 4 Drawing Sheets

(56) References Cited

U.S. PATENT DOCUMENTS

| | | | |
|---|---|---|---|
| 7,189,251 B2* | 3/2007 | Kay | A61B 17/0401 411/395 |
| 7,601,152 B2* | 10/2009 | Levy et al. | 606/63 |
| 7,909,825 B2 | 3/2011 | Saravia et al. | |
| 8,894,661 B2* | 11/2014 | McDevitt | A61B 17/809 606/104 |
| 9,060,809 B2* | 6/2015 | Tipirneni | A61B 17/683 |
| 2002/0032444 A1* | 3/2002 | Mische | 606/63 |
| 2002/0143333 A1* | 10/2002 | von Hoffmann et al. | 606/67 |
| 2004/0078084 A1* | 4/2004 | Albertorio | A61F 2/3601 623/23.26 |
| 2004/0097943 A1* | 5/2004 | Hart | A61B 17/686 606/232 |
| 2004/0147957 A1* | 7/2004 | Pierson, III | A61B 17/0469 606/228 |
| 2005/0187613 A1* | 8/2005 | Bolduc et al. | 623/1.23 |
| 2008/0255560 A1* | 10/2008 | Myers et al. | 606/62 |
| 2008/0269746 A1 | 10/2008 | Justin | |
| 2009/0118776 A1* | 5/2009 | Kelsch | A61B 17/0401 606/325 |
| 2009/0143781 A1 | 6/2009 | Mische | |
| 2009/0182336 A1* | 7/2009 | Brenzel et al. | 606/62 |
| 2010/0023010 A1 | 1/2010 | Nelson et al. | |
| 2010/0256690 A1* | 10/2010 | Appenzeller | A61B 17/8057 606/305 |
| 2010/0312292 A1* | 12/2010 | Tipirneni | A61B 17/92 606/86 R |
| 2011/0034925 A1* | 2/2011 | Tipirneni et al. | 606/62 |
| 2012/0239038 A1* | 9/2012 | Saravia et al. | 606/64 |
| 2013/0178899 A1* | 7/2013 | Chang et al. | 606/232 |
| 2014/0058391 A1* | 2/2014 | Appenzeller et al. | 606/62 |
| 2015/0250503 A1* | 9/2015 | Tipirneni | A61B 17/685 606/62 |

OTHER PUBLICATIONS

DE3835682, Apr. 1990, Andrejewski, A61B 17/58, English machine translation document.*

* cited by examiner

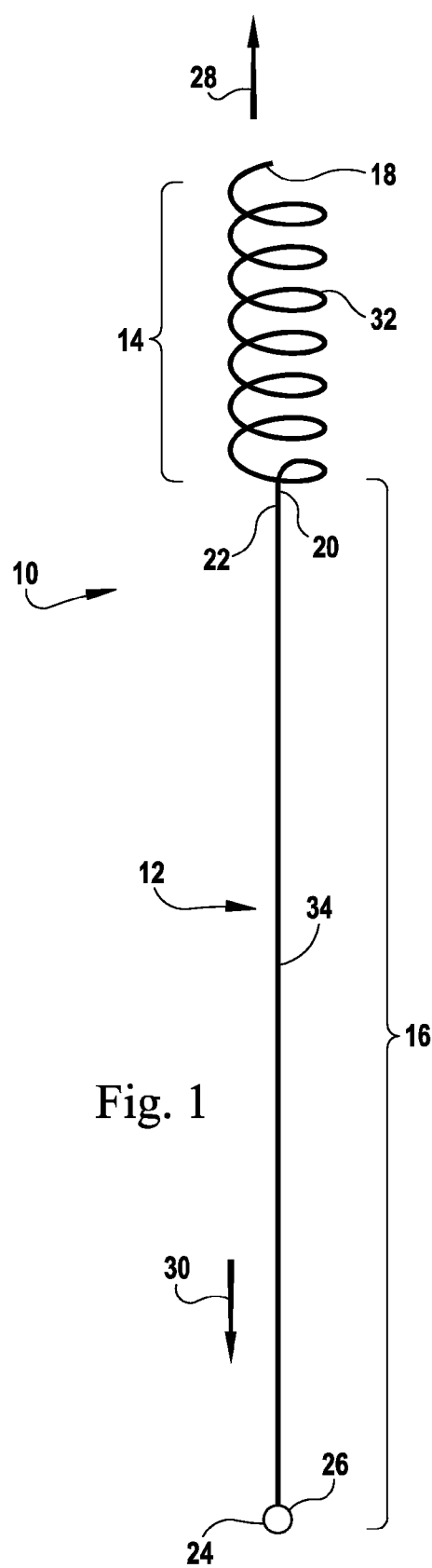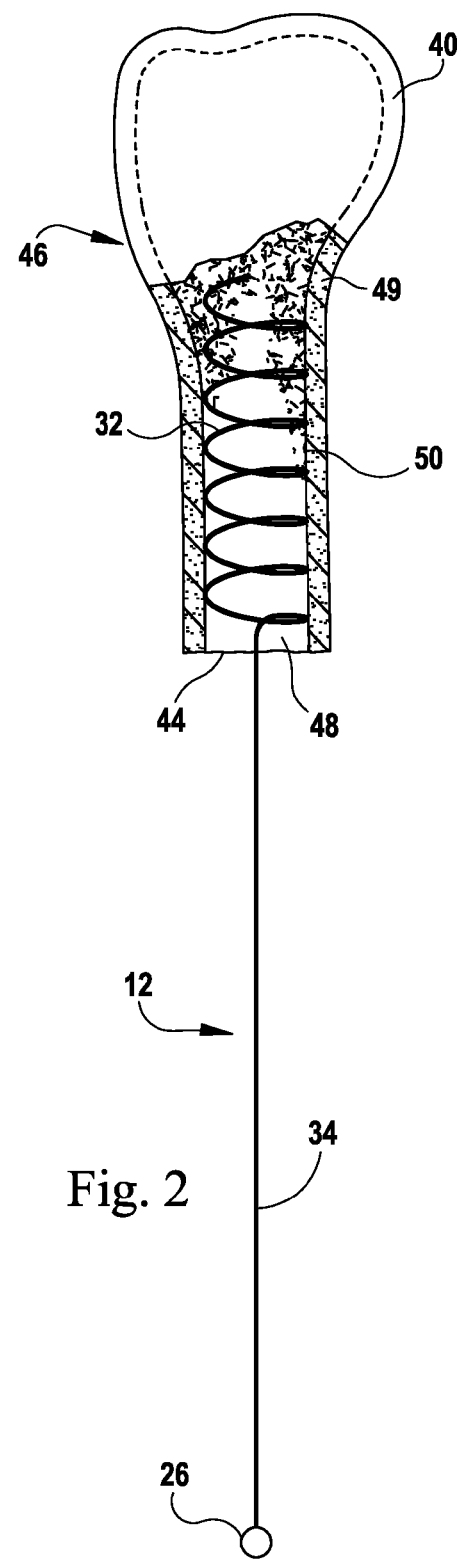

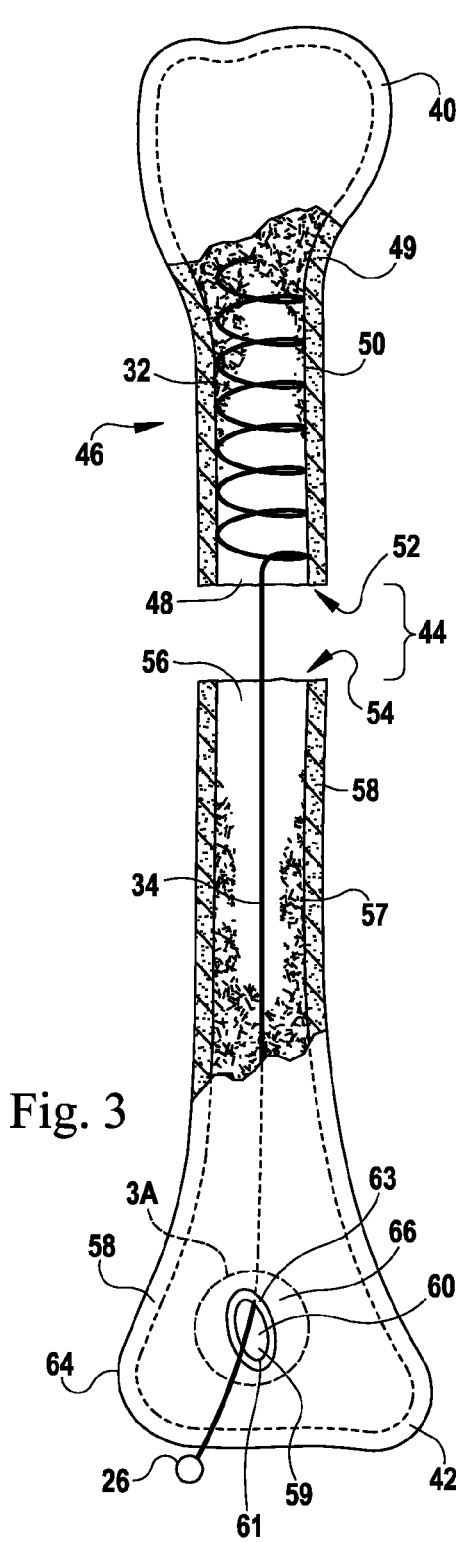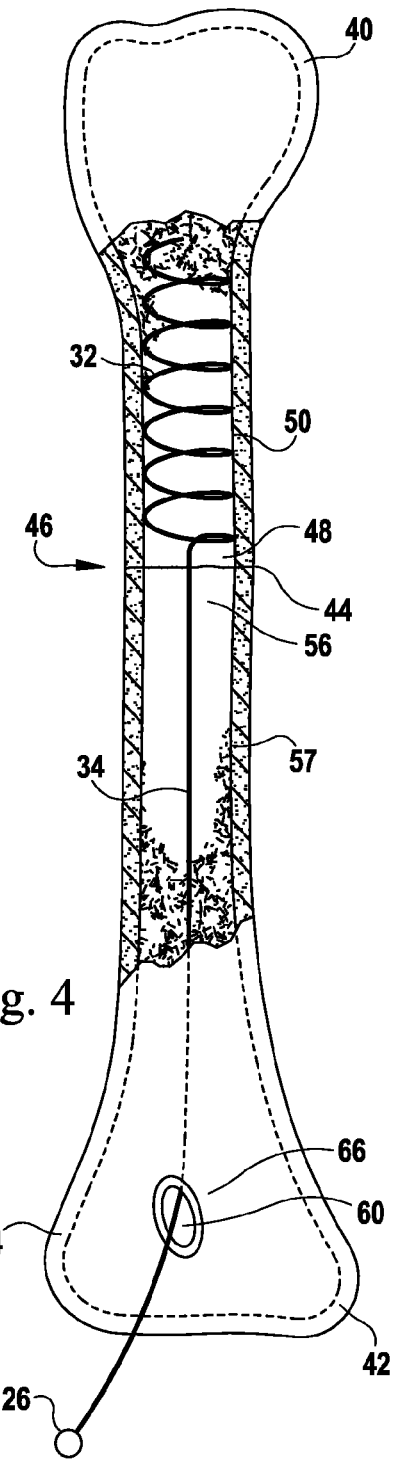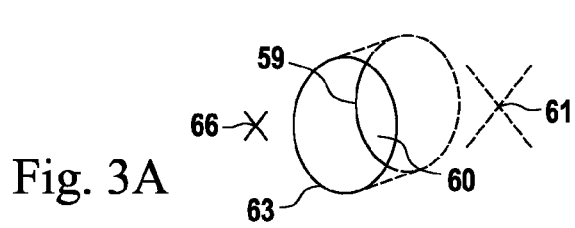
Fig. 3
Fig. 3A
Fig. 4

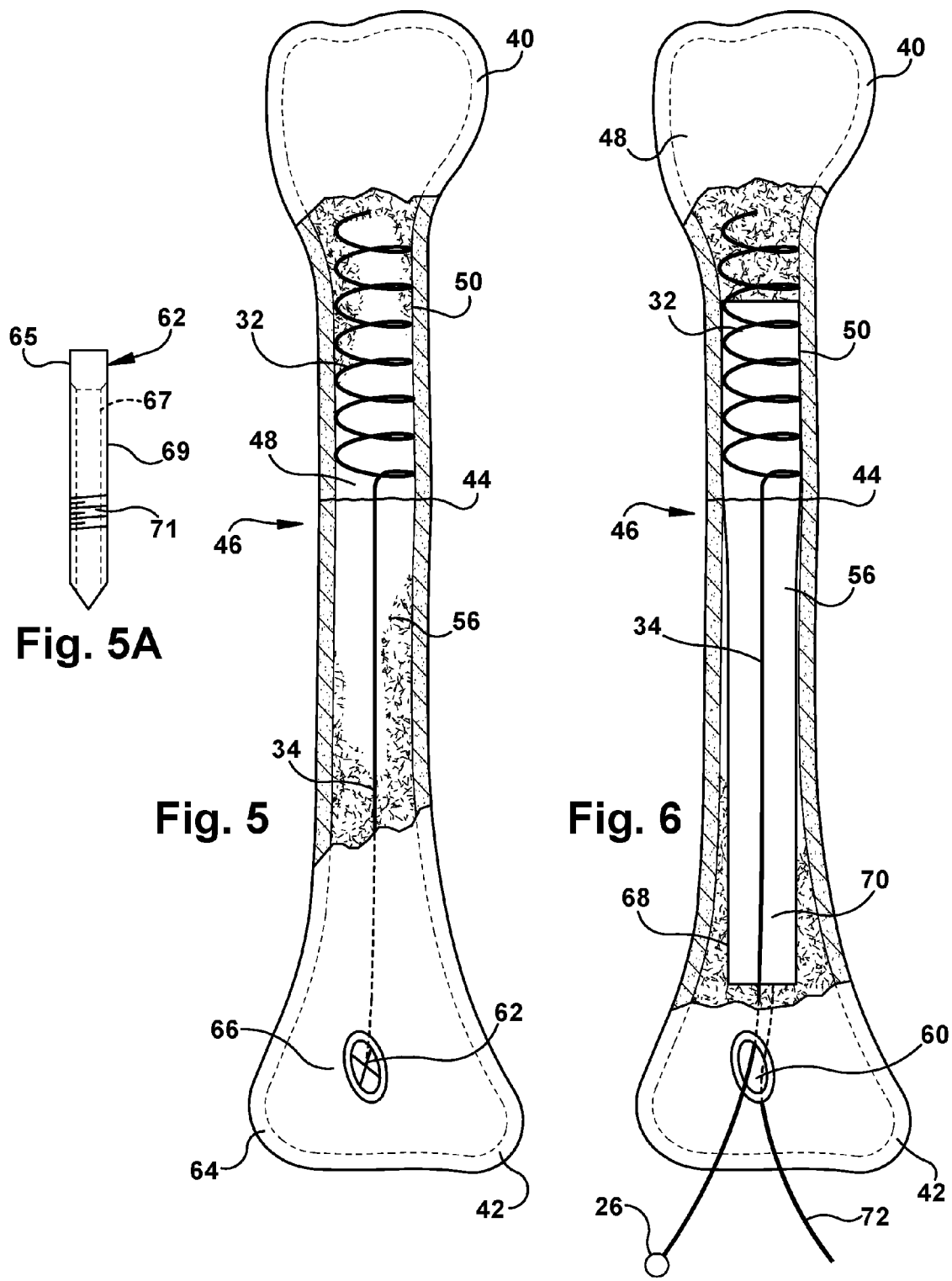

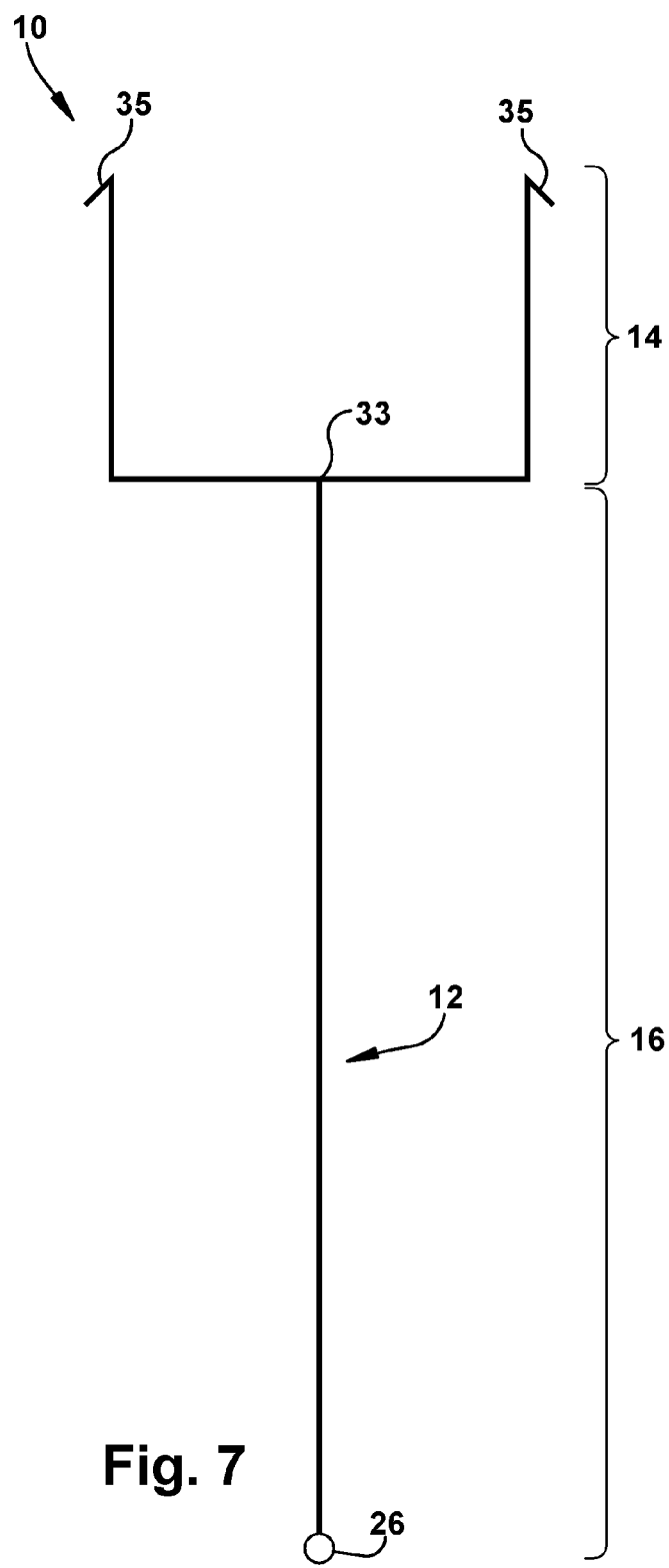
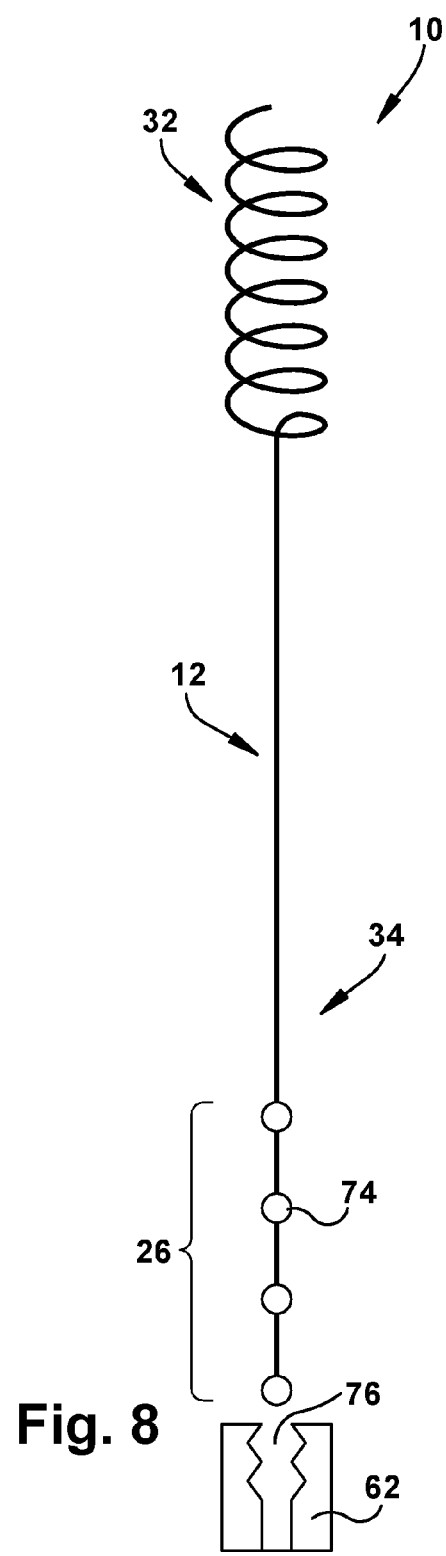

INTRAMEDULLARY BONE STENT

CROSS-REFERENCE TO RELATED APPLICATION

This application claims the benefit of U.S. Provisional Patent Application No. 61/665,949, filed Jun. 29, 2012 and entitled INTRAMEDULLARY BONE STENT, which is incorporated herein by reference in its entirety.

TECHNICAL FIELD OF THE INVENTION

The present invention relates to a device to promote healing of a fractured bone and, more particularly, to a device to apply compression to pieces of a fractured bone.

BACKGROUND OF THE INVENTION

Bone fixation devices are used to help heal a fracture by stabilizing the pieces of the fractured bone. Bone fixation devices may be external or internal devices. An internal bone fixation device may be engaged with an intramedullary portion of one of the bone pieces to hold the bone pieces in position while the fracture heals. Such an internal bone fixation device may also be used to reduce the fracture.

SUMMARY OF THE INVENTION

The present invention is directed to a device to promote healing of a fractured bone and, more particularly, to a device to apply compression to pieces of a fractured bone.

In accordance with an embodiment of the present invention, a bone fixation device comprises an elongated body. The elongated body includes a first end portion, which includes a coil, and an opposite second end portion, which includes an elongated tail. The second end portion also includes an attachment portion configured for engagement with a fastener.

In accordance with another embodiment of the present invention, a method of promoting healing of a fractured bone uses a bone fixation device. The bone fixation device comprises an elongated body including a first end portion formed as a coil and an opposite second end portion formed as an elongated tail. The second end portion includes an attachment portion configured for engagement with a fastener. The method comprises the step of inserting the first end portion of the elongated body into an intramedullary portion of a first bone piece such that the first end portion engages a wall of an intramedullary canal of the first bone piece. The method also comprises the step of extending the second end portion of the elongated body from the intramedullary portion of the first bone piece, across a bone fracture, and into an intramedullary canal of a second bone piece. The method further comprises the steps of passing the attachment portion of the second end portion of the elongated body into an opening formed in cortical tissue of the second bone piece, and fixing the attachment portion to an extramedullary portion of the second bone piece with a fastener.

BRIEF DESCRIPTION OF THE DRAWINGS

The foregoing and other features and advantages of the present invention will become apparent to one skilled in the art upon consideration of the following description of the invention and the accompanying drawings, in which:

FIG. 1 is a plan view of a bone fixation device in accordance with the present invention;

FIG. 2 is a schematic plan view of the bone fixation device of FIG. 1 with its first end portion installed in the intramedullary portion of a first bone piece;

FIG. 3 is a schematic plan view of the bone fixation device of FIG. 2 with its second end portion installed in the intramedullary portion of a second bone piece;

FIG. 3A is a schematic plan view of a passage formed in the second bone piece;

FIG. 4 is a schematic plan view of the bone fixation device of FIG. 3 with the first and second bone pieces having been brought together;

FIG. 5 is a schematic plan view of the bone fixation device of FIG. 4 with its second end portion fixed to a bone piece with a fastener;

FIG. 5A is a side view of a representative fastener used in the bone fixation device of FIG. 5;

FIG. 6 is a schematic plan view of the bone fixation device of FIG. 1 with the bone fixation device deployed within intramedullary portions of bone pieces with a sheath;

FIG. 7 is a plan view of an alternative embodiment of the bone fixation device of FIG. 1; and FIG. 8 is a schematic plan view of an alternative bone fixation device of FIG. 1 showing a proposed engagement of the second end portion of the device and a fastener.

DETAILED DESCRIPTION OF THE INVENTION

FIG. 1 shows a bone fixation device 10 in accordance with an example of the present invention. The bone fixation device 10 comprises an elongated body 12. The elongated body 12 is made of a relatively rigid biocompatible material, such as medical grade stainless steel, titanium, or nitinol.

The elongated body 12 includes a first end portion 14 and an opposite second end portion 16. The first end portion 14 includes a first end 18 and a second end 20. The second end portion 16 includes a first end 22 and a second end 24. The first end 22 of the second end portion 16 adjoins the second end 20 of the first end portion 14. The first end portion 14 of the elongated body 12 extends away from the second end portion 16 of the elongated body 12 in a first direction 28. Similarly, the second end portion 16 of the elongated body 12 extends away from the first end portion 14 of the elongated body 12 in a second direction 30 opposite the first direction 28.

The first end portion 14 of the elongated body 12 includes a coil 32. The coil 32 extends from the first end 18 of the first end portion 14 to the second end 20 of the first end portion 14. The coil 32 is configured to engage a bone piece or bone fragment and, more particularly, an intramedullary portion of a bone piece or a bone fragment. As used herein, the term "bone piece" has the same meaning as "bone fragment," in that these terms refer to a fractured portion of a bone. The first end portion 14 can have alternative configurations. FIG. 7 shows that the first end portion 14 can include a U-shaped portion 33. Hook portions 35 may be located at the ends of the U-shaped portion 33 to engage a portion of the bone piece.

The second end portion 16 of the elongated body 12 includes an elongated tail 34. The elongated tail 34 extends from the first end 22 of the second end portion 16 to the second end 24 of the second end portion 16. As shown, the elongated tail 34 has a generally straight or linear shape, which requires a shorter length of material to extend any specific distance. Alternatively, the elongated tail 34 may have another configuration, such as a curved or wavy shape. The elongated tail 34 is configured to extend through an intramedullary portion of a bone piece and out of a hole formed in cortical tissue of the bone piece.

The second end portion 16 also includes an attachment portion 26. As shown, the attachment portion 26 is disposed at the second end 24 of the second end portion 16 of the elongated body 12. The attachment portion 26 may alternatively be located at another position along the second end portion 16, spaced from the second end 24. The attachment portion 26 is configured to receive or engage a fastener (not shown in FIG. 1) when the bone fixation device 10 is installed or implanted in two or more bone pieces. As shown, the attachment portion 26 is a curved loop. The attachment portion 26 can alternatively have a rectangular shape, hook shape, or any other shape suitable to receive or engage a fastener. The attachment portion 26 is configured to be fixed to an extramedullary portion of a bone piece with the fastener.

In one example, the elongated body 12 is formed from a continuous length of wire with the first end portion 14 formed as the coil 32 and the second end portion 16 formed as the elongated tail 34. The wire may consist of a single strand of material or multiple strands of material. In another example, the elongated body 12 is formed from a single continuous filament of biocompatible material, such as a polymer material, with the first end portion 14 formed as the coil 32 and a second end portion 16 formed as the elongated tail 34. In a further example, the first end portion 14 is configured as a stent with a structure that includes a coil 32 and that also includes other structural features to provide, for example, a mesh structure.

The bone fixation device 10 may be used to promote healing of a fracture 44 between pieces 40, 42 of a bone 46. More particularly, the bone fixation device 10 may be used (a) to apply compression to the bone pieces 40, 42 to reduce the fracture 44 and (b) to fix the bone pieces 40, 42 in a desired alignment to promote healing of the fracture 44. Installation or implantation of the bone fixation device 10 involves inserting the bone fixation device 10 into intramedullary canals of the bone pieces 40, 42. As used herein, the term "intramedullary canal" has the same meaning as "medullary canal," "medullary cavity," and "marrow cavity," in that all of the foregoing terms refer to the intramedullary portion of a bone or bone piece. In use, the bone fixation device 10 is configured to extend from an intramedullary portion of one bone piece 40, across the fracture 44, and into an intramedullary portion of another bone piece 42.

FIGS. 2-5 show a method of promoting the healing of the fracture 44 in the bone 46 using the bone fixation device 10 of FIG. 1. The first step in the method is to insert the first end portion 14 of the bone fixation device 10 into an intramedullary canal 48 of the first bone piece 40. The first end portion 14 of the elongated body 12 is disposed on a first side 52 (FIG. 3) of the fracture 44. As shown in FIG. 2, the coil 32 of the first end portion 14 engages cortical tissue 49 that provides a wall 50 of the intramedullary canal 48. The wall 50 is generally tubular in shape and surrounds the intramedullary canal 48 to define the intramedullary canal. The engagement between the coil 32 of the first end portion 14 and the wall 50 holds the first end portion of the bone fixation device 10 in place within the intramedullary canal 48.

The coil 32 of the first end portion 14 of the elongated body 12 may engage the wall 50 of the intramedullary canal 48 through radially outwardly directed pressure on the wall or by penetrating into the wall or through a combination of pressure against the wall and penetration into the wall. Radially outwardly directed pressure on the wall 50 may be achieved by radially compressing or otherwise reducing the outer diameter of the coil 32 prior to inserting the coil into the intramedullary canal 48. After the coil 32 is properly positioned, the coil may be permitted to return to its original outer dimension and thereby press against the wall 50. In this regard, forming bone fixation device 10 or at least the coil 32 from nitinol, which has a shape memory that can be triggered by body heat, can facilitate the radial compression and expansion of the coil. The engagement between the coil 32 and the wall 50 must be sufficient to keep the coil from moving out of the intramedullary canal 48 of the first bone piece 40 when a tension load is applied to the bone fixation device 10, as explained in greater detail below.

After the coil 32 is installed or implanted within the first bone fragment or piece 40, the next step in the method is to install or implant the second end portion 16 of the bone fixation device 10 within the second bone piece 42. The second end portion 16 is extended across the fracture 44 away from the first end portion 14. As shown in FIG. 3, the elongated tail 34 of the second end portion 16 is then extended through an intramedullary canal 56 of the second bone piece 42. Cortical tissue 58 of the second bone piece 42 provides a wall 57 of the intramedullary canal 56. The wall 57 is generally tubular in shape and surrounds the intramedullary canal 56. Prior to the bone 46 being fractured and after the fracture 44 healing, the wall 50 and the wall 57 are joined in a single continuous wall, and the intramedullary canals 48 and 56 are portions of a single continuous intramedullary canal.

After the second end portion 16 is extended through the intramedullary canal 56, at least the attachment portion 26 is passed or extended into an opening 59 drilled or otherwise formed in an interior surface 61 of the wall 57 and the cortical tissue 58 of the second bone piece 42. The attachment portion 26 is further passed or extended through a passage 60 (FIG. 3A) extending between, and communicating with, the opening 59 and an opening 63 drilled or otherwise formed in an exterior surface 66 of the wall 57 and the cortical tissue 58. The elongated tail 34 is thereby disposed on a second side 54 of the fracture 44. The elongated tail 34 extends out of the second bone piece 42 through the opening 63 so that the attachment portion 26 of the second end portion 16 is positioned outside of the second bone piece.

Once the bone fixation device 10 has been installed within the bone pieces 40, 42, the next step in the method is to move at least one of the bone pieces 40, 42 with respect to the other bone piece. Tension is applied to the elongated body 12, by a surgeon or other user, until the bone pieces 40, 42 are arranged in a desired position relative to one another, such as their natural alignment with respect to each other. As shown in FIG. 4, after tension is applied to the elongated body 12 and the bone pieces 40, 42 have been moved relative to each other, the bone pieces 40, 42 contact each other at the location of the fracture 44. In one example, tension is applied to the coil 32, and the fracture 44 is reduced by manipulating the first bone piece 40 into its natural alignment using the coil 32. In another example, tension is applied to the elongated tail 34, and the fracture 44 is reduced by pulling the first bone piece 40 toward the second bone piece 42 and/or by moving the second bone piece 42 along the length of the elongated tail 34 toward the first bone piece 40. Compression is applied to each of the bone pieces 40, 42 after they contact each other using the bone fixation device 10 to promote healing of the fracture 44.

The final step in the method is to attach the second end portion 16 of the elongated body 12 to the second bone piece 42. Specifically, as shown in FIG. 5, the elongated tail 34 is fixed to an extramedullary portion 64 of the second bone piece 42 by a fastener 62 received in or otherwise engaged with the attachment portion 26 of the second end portion 16. The fastener 62 may be a screw, a nail, a tab, or a similar device to fix the attachment portion 26 of the second end portion 16 to the extramedullary portion 64 of the second bone piece 42 so that the attachment portion does not move lengthwise of the second bone piece. By way of example, FIG. 5A illustrates a fastener 62 in the form of a screw with an exterior surface 69, a head 65 and a shank or central shaft 67 having a spiral protrusion or thread 71. The fastener 62 extends into the attachment portion 26 and into the exterior surface 66 of the cortical tissue 58 and the second bone piece 42. The attachment portion 26 will thus extend around and engage the exterior surface 69 of the fastener 62, while the spiral protrusion or thread 71 will extend into and engage the cortical tissue 58 and the second bone piece. Fixing the attachment portion 26 to the second bone piece 42 helps to ensure that tension will be maintained on the bone fixation device 10, thereby helping to ensure that compression is maintained on the bone pieces 40, 42 and the fracture 44 and that the bone pieces remain in a desired position relative to one another. As shown, the fastener 62 extends into the opening 63 in the exterior surface 66 of the second bone piece 42. Alternatively, the fastener 62 may be secured to another portion of the second bone piece by, for example, extending into a screw hole (not shown) formed in the exterior surface 66.

Although the foregoing description presents installing the first end portion 14 in the first bone piece 40, extending the second end portion 16 across the fracture 44 and into the second bone piece 42, moving at least one of the bone pieces 40, 42 relative to the other, and fixing the second end portion 16 to the second bone piece 42 as four discrete and sequential steps in the method, two or more of the steps may be performed together. For example, the step of extending the second end portion 16 across the fracture 44 and into the second bone piece 42 and the step of moving one of the bone pieces 40, 42 toward the other may be performed simultaneously.

The method may also include installing the bone fixation device 10 within the bone pieces 40, 42 using a sheath 68, as shown in FIG. 6. The sheath 68 includes a sleeve 70 and a string 72. For purposes of installing the bone fixation device 10, both end portions 14 and 16 of the bone fixation device 10 are disposed within the sleeve 70, as shown. Alternatively, the first end portion 14, including the coil 32, may be the only portion of the bone fixation device 10 disposed within the sleeve 70. Prior to inserting the bone fixation device 10 into the sheath 68 and into the intramedullary canal 48, the outer diameter of the coil 32 is radially compressed or otherwise reduced to facilitate insertion of the coil into the intramedullary canal. The sheath 68 helps to retain the coil 32 in such a radially compressed condition. The sheath 68 and the enclosed bone fixation device 10 are then inserted into the intramedullary canals 48 and 56 of the first and second bone pieces 40 and 42, respectively. The string 72 extends out of the intramedullary canal 56 through the passage 60. Once the sheath 68 and the bone fixation device 10 are properly positioned within the intramedullary canals 48 and 56, the sleeve 70 is removed from the bone fixation device 10 and from the intramedullary canals 48, 56 by pulling on the string 72. The string 72 can be replaced by any other suitable device, such as an elongated strip of fabric or a length of wire, to facilitate removing the sleeve 70 from within the bone pieces 40, 42. After the sheath 68 is removed, the attachment portion 26 can be fixed to the extramedullary portion 64 of the second bone piece 42.

Although the fastener 62 may be a screw or a nail and the attachment portion 26 of the second end portion 16 of the elongated body 12 may be a loop, a hook or another structure configured to receive a screw or a nail, the attachment portion may alternatively be configured, for example, as a chain or string of beads 74 (FIG. 8) or an elongated, toothed ratchet (not shown). With such an alternative configuration, the fastener 62 may be in the form of an annular plug with a central opening 76 that receives the attachment portion 26. The annular plug 62 would resiliently snap over and engage successive beads 74 in the chain or string or successive teeth on the toothed ratchet to maintain tension on the bone fixation device 10 and maintain a compression load on the bone pieces 40 and 42. As another alternative, the second end portion 16 of the elongated body 12 may include a removable portion that extends beyond the attachment portion 26 away from the first portion 14 of the elongated body. Such a removable portion may be grasped by a hemostat or other clamping or gripping tool to help reduce the fracture 44 and/or maintain a compression load on the bone pieces 40 and 42 until the attachment portion 26 is secured with a fastener 62. The removable portion may then be trimmed off or otherwise removed.

From the above description of the invention, those skilled in the art will perceive improvements, changes, and modifications. Such improvements, changes, and/or modifications within the skill of the art are intended to be covered by the appended claims.

Having described the invention, the following is claimed:

1. A bone fixation device comprising:
   (a) an elongated body, the elongated body being a length of wire having a consistent thickness,
      a first end portion of the length of wire having said thickness being wound helically to form a single coil that throughout its extent intermediate opposed ends of the first end portion is free of any intersection with itself and any intersection with any other portion of the bone fixation device, the first end portion being configured to be disposed substantially on a first side of a bone fracture, and
      an opposite second end portion of the length of wire being formed as an elongated tail having said thickness with an attachment portion configured for engagement with a fastener, the elongated tail having a generally straight shape, the second end portion being configured to be disposed substantially on a second side of the bone fracture; and
   (b) a fastener having a central shaft with a thread configured to extend into and engage cortical tissue of a bone piece so as to be held in the bone piece,
      the attachment portion being configured as a loop so as to extend around and engage an exterior surface of the fastener when the thread of the fastener is extending into and engaging the cortical tissue of the bone piece, thereby to fix the second end portion of the length of wire to an extramedullary portion of the bone piece;
      wherein the first end portion and the second end portion extend along a longitudinal axis, the fastener being configured to extend through the loop transverse to said longitudinal axis.

2. The bone fixation device of claim 1, wherein the bone piece is a second bone piece, the first end portion of the elongated body being configured to be inserted into an intramedullary canal of a first bone piece such that the first end portion engages a wall of the intramedullary canal.

3. The bone fixation device of claim 2, wherein the coil is the sole mechanism for anchoring the bone fixation device within the intramedullary canal.

4. The bone fixation device of claim 1, wherein the first end portion of the elongated body extends from the second end portion of the elongated body in a first direction, and the second end portion of the elongated body extends from the first end portion of the elongated body in a second direction.

5. The bone fixation device of claim 1, wherein the bone piece is a second bone piece, the second end portion of the elongated body being configured to extend out of the intramedullary canal of the second bone piece through a hole formed into cortical tissue of the second bone piece.

6. The bone fixation device of claim 1, wherein the second end portion of the elongated body is configured to extend across a bone fracture.

7. The bone fixation device of claim 1, wherein the bone piece is a second bone piece, the bone fixation device being configured to extend from an intramedullary portion of a first bone piece, across a bone fracture, and into an intramedullary canal of the second bone piece.

8. The bone fixation device of claim 1, wherein the attachment portion of the second end portion of the elongated body is disposed at a terminal end of the second end portion.

9. The bone fixation device of claim 1, wherein the elongated body is configured to have tension applied to at least the second end portion during installation of the bone fixation device.

10. A bone fixation device comprising:
(a) an elongated body, the elongated body being a filament of biocompatible material having a consistent thickness,
a first end portion of the filament having said thickness being wound helically to form a single coil that throughout its extent intermediate opposed ends of the first end portion is free of any intersection with itself and any intersection with any other portion of the bone fixation device, the first end portion being configured to be disposed substantially on a first side of a bone fracture; and
an opposite second end portion of the filament being formed as an elongated tail having said thickness with an attachment portion configured for engagement with a fastener, the elongated tail having a generally straight shape, the second end portion being configured to be disposed substantially on a second side of the bone fracture; and
(b) a fastener having a central shaft with a thread configured to extend into and engage cortical tissue of a bone piece so as to be held in the bone piece,
the attachment portion being configured as a loop so as to extend around and engage an exterior surface of the fastener when the thread of the fastener is extending into and engaging the cortical tissue of the bone piece, thereby to fix the second end portion of the filament to an extramedullary portion of the bone piece;
wherein the first end portion and the second end portion extend along a longitudinal axis, the fastener being configured to extend through the loop transverse to said longitudinal axis.

11. A method of promoting healing of a fractured bone using the bone fixation device of claim 1, the method comprising the steps of:
inserting the first end portion of the elongated body into an intramedullary portion of a first bone piece such that the first end portion engages a wall of an intramedullary canal of the first bone piece;
extending the second end portion of the elongated body from the intramedullary portion of the first bone piece, across a bone fracture, and into an intramedullary canal of a second bone piece;
passing the attachment portion of the second end portion of the elongated body into an opening formed in cortical tissue of the second bone piece; and
fixing the attachment portion of the second end portion to an extramedullary portion of the second bone piece with the fastener.

12. The method of claim 11, further comprising the step of applying tension to the second end portion to cause the bone pieces to contact each other.

13. The method of claim 11, further comprising the step of deploying the bone fixation device into the intramedullary portion of the first bone piece within a sheath.

14. The method of claim 13, further comprising the step of removing the sheath from the bone fixation device after the bone fixation device is deployed into the intramedullary portion of the first bone piece.

15. The method of claim 11, further comprising the step of disposing the first end portion of the elongated body on a first side of the fracture.

16. The method of claim 11, further comprising the step of extending the fastener through an exterior surface of the second bone piece.

* * * * *